United States Patent [19]

Dorwald et al.

[11] Patent Number: 5,955,548
[45] Date of Patent: Sep. 21, 1999

[54] SUBSTITUTED 3, 3-DIAMINO-2-PROPENENITRILES, THEIR PREPARATION AND USE

[75] Inventors: Florenzio Zaragonza Dorwald, Herlev; John Bondo Hansen, Jyderup, both of Denmark

[73] Assignee: Novo Nordisk A/S, Bagsvaerd, Denmark

[21] Appl. No.: 09/072,096

[22] Filed: May 4, 1998

Related U.S. Application Data

[60] Provisional application No. 60/051,017, May 27, 1997.

[30] Foreign Application Priority Data

May 7, 1997 [DK] Denmark ................................. 0533/97

[51] Int. Cl.[6] ........................... C08F 20/56; C08G 77/38; C07C 229/30
[52] U.S. Cl. ..................... 525/329.4; 525/333.6; 525/355; 525/359.2; 525/359.3; 525/359.4; 525/374; 525/375; 525/379; 525/382; 525/383; 525/384; 525/420; 525/474; 525/523; 525/54.3; 525/54.31; 558/455
[58] Field of Search ........................ 558/455; 525/333.6, 525/355, 359.2, 359.3, 359.4, 374, 375, 379, 382, 383, 384, 420, 474, 523, 54.3, 54.31

[56] References Cited

U.S. PATENT DOCUMENTS 4,024,260  5/1977  Durant et al. .
4,277,485  7/1981  Durant et al. .

FOREIGN PATENT DOCUMENTS 0 010 396  4/1980  European Pat. Off. .
0 547 517  6/1993  European Pat. Off. .
0 591 891  4/1994  European Pat. Off. .
2.229.417  12/1974  France .

OTHER PUBLICATIONS

Klemm et al., Chem. Ber., vol. 114, pp. 2001–2018 (1981).
Thompson et al., Chem. Rev., vol. 96, pp. 555–600 (1996).
Chemical Abstract No. 73:98434, vol. 73, No. 19, (Nov. 9, 1970).

*Primary Examiner*—Johann Richter
*Assistant Examiner*—Ebenezer Sackey
*Attorney, Agent, or Firm*—Steve T. Zelson; Carol E. Rozek

[57] ABSTRACT

Substituted cyanoenamines of the formula I

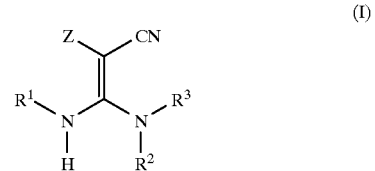

wherein Z, $R^1$, $R^2$ and $R^3$ are defined in the description, compositions thereof and methods for preparing the compounds are disclosed. The compounds are useful in the treatment of diseases of the central nervous system, the cardiovascular system, the pulmonary system, the gastrointestinal system and the endocrinologic system.

6 Claims, No Drawings

SUBSTITUTED 3, 3-DIAMINO-2-PROPENENITRILES, THEIR PREPARATION AND USE

CROSS-REFERENCE TO RELATED APPLICATIONS

This application claims priority of provisional application Ser. No. 60/051,017 filed May 27, 1997 and claims priority under 35 U.S.C. 119 of Danish application serial no. 0533/97 filed May 7, 1997, the contents of which are fully incorporated herein by reference.

FIELD OF THE INVENTION

The present invention relates to substituted 3,3-diamino-2-propenenitriles, in the following also referred to as cyanoenamines, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinological system.

BACKGROUND OF THE INVENTION

Potassium channels play an important role in membrane potential. Among the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic-cells, skeletal muscles, smooth muscles, central neurones and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulfonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hair growth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labour.

Since some $K_{ATP}$-openers are able to antagonize vasospasms in basilar or cerebral arteries the compounds of the present invention can be used for the treatment of vasospastic disorders such as subarachnoid hemorrhage and migraine.

Potassium channel openers hyperpolarize neurons and inhibit neurotransmitter release and it is expected that the present compounds can be used for the treatment of various diseases of the central nervous system, e.g. epilepsia, ischemia and neurodegenerative diseases, and for the management of pain.

Recently, it has been shown that diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. Biochem. Pharmacol, 47, 1381–1386 (1994); Pirotte B. et al., J. Med. Chem., 36, 3211–3213 (1993). Diazoxide has furthermore been shown to delay the onset of diabetes in BB-rats (Vlahos W D et al. Metabolism 40, 39–46 (1991). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that such potassium channel openers can be used for treatment of diseases characterised by an overproduction of insulin and for the treatment and prevention of diabetes.

DESCRIPTION OF THE INVENTION

The present invention relates to substituted 3,3-diamino-2-propenenitriles, in the following also referred to as cyanoenamines, of the general formula I:

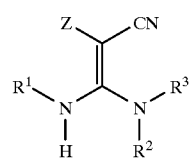

I wherein $R^1$ is alkyl optionally substituted with halogen, hydroxy, alkoxy, aryloxy, alkylthio, arylthio, dialkylamino, arylalkylamino or diarylamino; aralkyl, aryl optionally substituted with alkyl, trifluoromethyl, aryl, heteroaryl, halogen, alkoxy, aryloxy, dialkylamino, alkylarylamino, diarylamino, nitro, alkyl-sulfonyl, aryl-sulfonyl, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxycarbonyl or aminocarbonyl;

$R^2$ and $R^3$ are independently hydrogen, alkyl optionally substituted with aryl, heteroaryl, a 5-,6- or 7-membered heterocyclic system, halogen, hydroxy, alkoxy, aryloxy, alkylthio, arylthio, dialkylamino, arylalkylamino or diarylamino; aryl, optionally substituted with alkyl, aryl, heteroaryl, halogen, alkoxy, aryloxy, dialkylamino, alkylarylamino, diarylamino, nitro, alkyl-sulfonyl, aryl-sulfonyl, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxycarbonyl or aminocarbonyl;

or $R^2$ and $R^3$ are linked together by —$(CH_2)_n$—, n being 4–7, provided that $R^2$ and $R^3$ cannot be hydrogen at the same time;

Z is hydrogen, cyano, alkoxycarbonyl, optionally substituted aminocarbonyl, alkylsulfonyl or arylsulfonyl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxy-carbonyl or aminocarbonyl; and pharmaceutically acceptable salts thereof.

Within its scope the invention includes all diastereomers and enantiomers of compounds of formula I, some of which are optically active, and also their mixtures including racemic mixture thereof.

The scope of the invention also includes all tautomeric forms of the compounds of formula I.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in *Journal of Pharmaceutical Science*, 66, 2 (1977) and incorporated herein by reference, or lithium, sodium, potassium, magnesium and the like.

The term "5-,6- or 7-membered heterocyclic system" as used herein refers to: a monocyclic unsaturated or saturated system containing one, two or three hetero atoms selected from nitrogen, oxygen and sulfur and having 5 members, e.g. pyrrole, furan, thiophene, pyrroline, dihydrofuran, dihydrothiophene, imidazole, imidazoline, pyrazole, pyrazoline, oxazole, thiazole, isoxazole, isothiazole, 1,2,3-oxadiazole, furazan, 1,2,3-triazole, 1,2,3-thiadiazole or 2,1,3-thiadiazole; an aromatic monocyclic system containing two or more nitrogen atoms and having 6 members, e.g. pyrazine, pyrimidine, pyridazine, 1,2,4-triazine, 1,2,3-triazine or tetrazine; a non-aromatic monocyclic system containing one or more hetero atoms selected from nitrogen, oxygen and sulfur and having 6 or 7 members, e.g. pyran, thiopyran, piperidine, dioxane, oxazine, isoxazine, dithiane, oxathine, thiazine, piperazine, thiadiazine, dithiazine, oxadiazine or oxoazepane.

Alkyl refers to lower straight, cyclic, bicyclic, fused or branched alkyl having 1 to 15 carbon atoms, preferentially 1 to 6 carbon atoms. Aryl refers to phenyl or phenyl substituted with alkyl or phenyl, or phenyl fused with cycloalkyl, or polycyclic aromatic systems such as naphthyl, anthracenyl, phenanthrenyl, fluorenyl, etc. Alkylene refers to lower straight, cyclic, fused or branched alkylene having 1 to 15 carbon atoms, preferentially 1 to 6 carbon atoms. Heteroaryl refers to any of the possible isomeric, unsubstituted or alkyl-substituted pyrrolyl, furyl, thienyl, imidazolyl, pyrazolyl, triazolyl, tetrazolyl, oxazolyl, thiazolyl, oxadiazolyl, thiadiazolyl, pyridyl, pyrazinyl, pyrimidinyl and pyridazinyl, as well as the corresponding benzo and dibenzo derivatives or other fused ring-systems thereof. Heteroaryl is also intended to mean the partially or fully hydrogenated derivatives of the heterocyclic systems enumerated above. Alkoxy refers to —O-alkyl and aryloxy refers to —O-aryl. Cyano refers to —CN, hydroxy refers to —OH, amino refers to —$NH_2$ and nitro refers to —$NO_2$. Dialkylamino refers to —N(alkyl)$_2$. Alkylarylamino refers to —N(alkyl)(aryl) and diarylamino refers to —N(aryl)$_2$. Halogen refers to —F, —Cl, —Br and —I. Aralkyl refers to -alkylene-aryl. Alkylthio refers to —S-alkyl and arylthio refers to —S-aryl. Alkoxycarbonyl refers to —CO—O-alkyl and aminocarbonyl refers to —CO—N(alkyl)$_2$, —CO—N(alkyl)(aryl) or —CO—N(aryl)$_2$. Acylamino refers to —N(alkyl)—CO-alkyl or —N(alkyl)—CO-aryl. A leaving group refers to a group or atom capable of existing in solution as a negatively charged species, or a positively charged group or atom.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

The compounds of the present invention may also be used for the treatment of diseases associated with decreased skeletal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the ureter. Potassium channel openers also relax urinary bladder smooth muscle, thus, the compounds of the present invention can be used for the treatment of urinary incontinence.

The present compounds could also be used for treatment of conditions associated with disturbances in gastrointestinal mobility such as irritable bowel syndrome. Additionally these compounds can be used for the treatment of premature labor and dysmenorrhea.

Further, potassium channel openers promote hairgrowth, therefore, the compounds of the present invention can be used for the treatment of baldness.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers and hence the compounds of the present invention can be used for counteracting the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce betacell rest which may prevent the progression of the autoimmune disease.

Compounds of the present invention which act as blockers of $K_{ATP}$-channels can be used for the treatment of NIDDM.

Preferably, the compounds of the present invention may be used for treatment or prevention of diseases of the endocrinological system such as hyperinsulinemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

In yet another aspect, the present invention relates to methods of preparing the above mentioned compounds. The methods comprise solid phase and combinatorial synthesis of organic compounds, and most particularly, a therapeutically important class of compounds, namely differently substituted cyanoenamines, useful as potassium channel openers. The new synthetic sequence disclosed in this invention gives access to a new class of cyanoenamines, useful as potassium channel openers.

The following terms are intended to have the following, general meanings:

1. Substrate: refers to any insoluble or partially insoluble material, to which compounds may be covalently attached. Substrates may be selected from the group consisting of any kind of organic or inorganic polymeric or oligomeric compound, e.g. polystyrene with different grades of crosslinking, polyethylene glycol (PEG), polyethylene glycol attached to polystyrene (e.g. TentaGel), polyacrylamides, polyamides, polysaccharides or silicates. Optionally, a given portion of substrate may be attached to a tag, i.e. a material or device which permits the unambiguos identification of this portion of substrate within a plurality of portions of substrate.

2. Linker: a molecule with at least two reactive sites, which permit its covalent attachment to other molecules or to a substrate. Either the bond of the linker to the substrate or the bond of the linker to other molecules attached to it or the linker itself must be cleavable upon selective exposure to an activator such as a selected chemical activator or other specific conditions, e.g. by treatment with a strong acid or by exposure to electromagnetic radiation or by metal catalysis.

3. Array: A collection of N single compounds or N mixtures of compounds with a common structural element, synthesized simultaneously in a parallel fashion using the same synthetic reaction sequence. The precise structure of a single compound within an array of compounds or the components of a mixture within an array of mixtures is determined by the sequence of reactants which gave rise to this compound or mixture and can be deduced from the recorded reaction-protocol. The spatial arrangement of the array is irrelevant.

4. Cyanoenamine: Organic compound containing the structural element RR'N—CR''=CR'''—CN.

5. Protecting group: A material which is chemically bound to a molecule or a substrate and which may be removed upon selective exposure to an activator such as a selected chemical activator or other specific conditions, e.g. by treatment with a strong acid or by exposure to electromagnetic radiation or by metal catalysis.

6. Combinatorial synthesis: An ordered strategy for parallel synthesis of arrays of single compounds or mixtures, by sequential addition of reagents.

7. Abbreviations: The following frequently used abbreviations are intended to have the following meanings:
AcOH: glacial acetic acid
DBU: 1,8-diazabicyclo[5.4.0]undec-7-ene
DCM: dichloromethane, methylenechloride
DIC: diisopropylcarbodiimide
DMF: N,N-dimethyl formamide
EDC: N-ethyl-N'-(3-dimethylaminopropyl)carbodiimide hydrochloride, "water-soluble carbodiimide"
FMoc: fluorenylmethyloxycarbonyl
NMP: N-Methylpyrrolidone
R: organic radical
TFA: trifluoroacetic acid
THF: tetrahydrofuran The method for the synthesis of therapeutically useful compounds is also provided by virtue of the present invention. The invention also provides a rapid approach for combinatorial synthesis and screening of arrays of cyanoenamine derivatives as a therapeutically important class of compounds. The invention also provides a solid phase synthesis of cyanoenamines, which eliminates purification and isolation steps and thus highly increases synthesis efficiency. The specification also describes an important extension of solid phase synthesis methods to nonoligomeric organic compounds.

A further understanding of the nature and advantages of the invention may be realized by reference to the remaining portions of the specification.

The application of the present invention also includes the rapid preparation and screening, preferably in parallel and simultaneous fashion, of a large number of differently substituted cyanoenamines of the general formula I

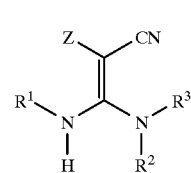

I wherein

Z, $R^1$, $R^2$ and $R^3$ are as defined above or of the general formula II

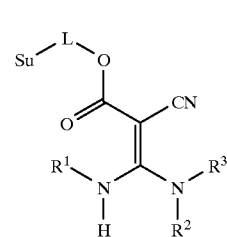

II wherein

Su is a substrate,

L is a chemical bond or a linker, $R^1$, $R^2$ and $R^3$ are as defined above.

An overall illustration of the solid phase synthesis of cyanoenamines is shown in reaction Scheme 1.

Scheme 1

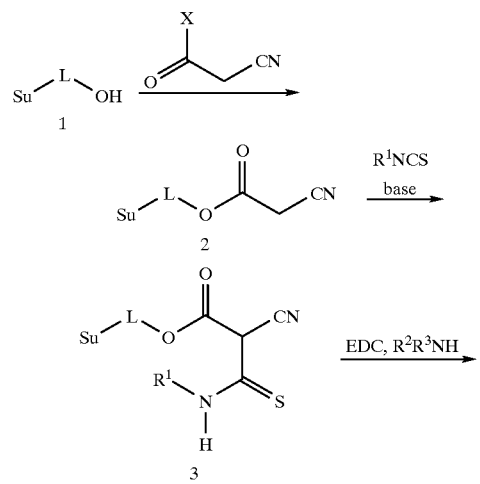

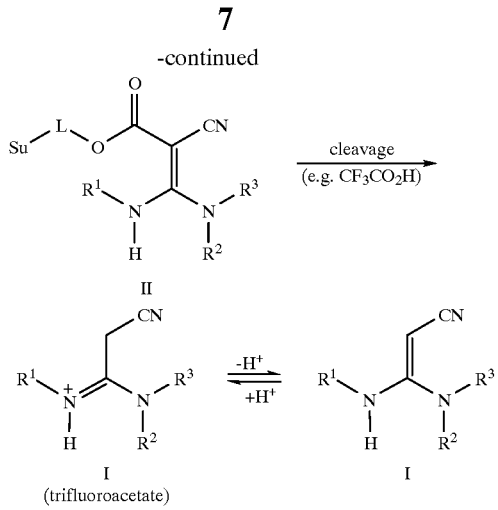

In this synthesis, the substrate Su may be any insoluble or partially insoluble material, to which compounds may be covalently attached. Preferentially, the substrates may be selected from the group consisting of polystyrene, polyethylene glycol (PEG), polyethylene glycol attached to polystyrene (e.g. TentaGel), polyamides, polysaccharides and silicates. Depending on the type of substrate chosen, different types of solvents or protecting groups may be used.

The substrate-bound alcohol 1 may be acylated with an appropriate cyanoacetic acid derivative of the general structure NC—CH$_2$—COX, X being a leaving group, preferentially with the in situ generated symmetric anhydride (Zaragoza, F. Tetrahedron Lett. 1995, 36, 8677–8678). Alternatively, other, in situ generated or isolated derivatives of cyanoacetic acid may be used as acylating reagents, such as the mixed anhydrides derived from alkyl chloroformates and cyanoacetic acid, or the imidazolide or other types of activated esters, such as the N-hydroxybenzotriazolyl ester or N-hydroxysuccinyl ester or other activated esters, obvious to those skilled in the art. The esterification reaction can optionally be carried out in the presence of a catalyst, e.g. 4-dimethylaminopyridine, to yield a derivative of the general formula {substrate}-{linker}—O—CO—CH$_2$—CN.

The resulting, resin bound cyanoacetic acid derivative 2 may then be treated with an excess of an aromatic or aliphatic isothiocyanate of the general structure R$^1$—NCS in an appropriate solvent such as NMP, DMF or THF, in the presence of a base, preferentially diisopropylethylamine or 1,8-diazabicyclo[5.4.0]undec-7-ene (DBU).

The resulting intermediate product 3 may then be treated with EDC and a primary or secondary aliphatic or aromatic amine of the general structure R$^2$R$^3$NH in a suitable solvent, such as NMP, DMF, acetonitrile, DCM, 1,2-dichloroethane, toluene, ethyl acetate, etc., preferentially in DMF. Alternatively, other condensing agents may be used (e.g. benzotriazole-1-yl-oxy-tris-(dimethylamino)phosphonium hexafluorophosphate ("BOP"), carbonyldiimidazole, N-ethyl-N'-(3-trimethylammoniumpropyl)-carbodiimide, diisopropylcarbodiimide, dicyclohexylcarbodiimide, etc.), alone or in the presence of a catalyst such as pyridinium tosylate or salts of tertiary amines. This reaction is closely related to a published procedure for the conversion of thioureas to cyanoguanidines (K. S. Atwal, S. Z. Ahmed, B. C. O'Reilly, Tetrahedron Lett. 1989, 30, 7313–7316).

Cleaving of the linker of the substrate-bound cyanoenamine II may release the cyanoenamine derivative I into solution. Cleavage conditions will depend upon the type of substrate and linker chosen. E. g., in the case of a polystyrene resin with a Wang linker or a Rink linker, treatment of the support-bound cyanoenamine II with neat TFA or TFA/DCM mixtures may lead to a cleavage of the linker. Thereby the cyanoenamine I may result as its cyanoamidine-trifluoroacetate tautomer, which may tautomerize reversibly into the neutral cyanoenamine when treated with bases or a buffer.

Alternatively, further chemical transformations may be carried out with the cyanoenamine derivatives II. Those cyanoenamines II which contain a NH-group may be acylated at nitrogen by treatment with an excess of an activated carboxylic acid derivative or with an isocyanate or with an isothiocyanate or with a sulfonylchloride, to yield the corresponding carboxamides, ureas, thioureas or sulfonamides, respectively. Each of these reactions may be performed by conventional means, readily apparent to those skilled in the art.

Alternatively, further chemical transformations may be carried out with the cyanoenamine derivatives I, which give high yields and pure crude products, so that no further purification of these derivatives will be required for their screening. For instance, those cyanoenamine derivatives which contain a NH-group may be acylated at nitrogen by treatment with an excess of an activated carboxylic acid derivative or with an isocyanate or with an isothiocyanate or with a sulfonylchloride, to yield the corresponding carboxamides, ureas, thioureas or sulfonamides, respectively. Each of these reactions may be performed by conventional means, readily apparent to those skilled in the art.

Using this synthetic method, arrays of cyanoenamine derivatives II or I may be constructed with the help of a device for parallel solid phase synthesis. This may be either the pin method developed by Geysen et al. (J. Immunol. Meth. 1987, 102, 259–274) or a device with several reactors for solid phase synthesis (containers with a permeable wall), which permits the automated or manual addition of reagents and solvents, as well as the removal of the solvents from the reactors by simultaneous or individual application of a pressure difference between the inside and the outside of the permeable wall of the reactors.

Such an array may be prepared on a multiple organic synthesizer (e.g. "ACT 496" of "Advanced ChemTech") by individually reacting under the conditions specified below a cyanoacetylated substrate located in individual containers, with different isothiocyanates of the general structure R$^1$—NCS in the presence of a base. The resulting intermediates 3 may then be reacted with different amines of the general structure R$^2$R$^3$NH in DMF in the presence of EDC to give an array of different cyanoenamine derivatives II. Cleavage from the support will provide an array of the corresponding cyanoenamines I.

The present invention also provides the synthesis of arrays of mixtures of cyanoenamine derivatives. This can be achieved either by the "split and mix" method (Sepetov, N. F., Krchnák, V., Stankova, M., Wade, S., Lam, K. S., and Lebl Proc. Natl. Acad. Sci. USA 1995, 92, 5426–5430) or by using mixtures of the corresponding reagents.

By virtue of the present invention basically two different types of arrays of cyanoenamines I or II may be constructed: fully combinatorial arrays (FCA) and not-fully combinatorial arrays (NFCA).

By FCA we refer to arrays of substituted cyanoenamines, in which all the possible combinations of a set of selected building blocks (R-groups) are realized. As an example, a FCA of N cyanoenamines may be prepared by selecting n isothiocyanates and m amines so that n×m=N, and synthesizing all the possible combinations of isothiocyanate/ amine. The selection of building blocks may be done with regard to the expected properties of the members of the array.

By NFCA we refer to arrays of cyanoenamines, in which only a selection of all the possible combinations of a set of selected building blocks is realized. As an example, a NFCA of N cyanoenamines may be prepared by first selecting n isothiocyanates and m amines so that n×m>N. Then a selection of N cyanoenamines from all the n×m theoretically possible cyanoenamines is done by grouping all the n×m possible cyanoenamines into N groups of cyanoenamines with similar expected properties and selecting from each of these groups one cyanoenamine, which is then synthesized. The selection of building blocks and of cyanoenamines may be done with regard to the expected properties of the members of the array. For the preparation of such arrays of compounds, the exact positions of the substrate does, by itself, not give any structural information about the compound prepared on this particular batch of substrate. For this reason, the spatial arrangement of the substrate is irrelevant. Structural information will be accessible from the records of the sequences of reagents added to each batch of substrate. In every step of the preparation of a FCA or a NFCA, the exact location of one substrate-container within the array of containers and the structure of the different reagents added to this container is recorded, so that the precise structure of the cyanoenamine resulting from one given container can always be deduced.

The resulting arrays of cyanoenamines may then be screened by comparing the individual cyanoenamines in terms of their ability to bind to a particular receptor or to induce a particular biological process or to catalyze a biochemical or chemical reaction. This can be achieved basically in two different ways. One possibility may be the screening of the substrate-bound cyanoenamines II, e.g. against a soluble receptor. This could for instance be a radioactively labelled peptide or enzyme, which would easily permit to determine the binding-strength of a given substrate-bound cyanoenamine II to this peptide by washing away the excess of radioligand used and determining the remaining radioactivity of each substrate-bound cyanoenamine II-peptide complex. Alternatively, as a further example, catalytic activity of the different substrate-bound cyanoenamines II for a given biological process or a chemical reaction may be measured by comparing the speed at which this biological process or a chemical reaction takes place in the presence and in the absence of a given substrate-bound cyanoenamine II.

The second option for screening may consist in screening the cyanoenamines I, after having cleaved the linker of the substrate-bound cyanoenamines II and using appropriately charged and indexed Microtiter plates of similar multiwell arrangements, in solution against an optionally substrate-bound receptor or enzyme. The screening of soluble small molecules is conventional and well known. Typically, radioassays are being used, in which the competitive binding of the radiolabelled, natural ligand of a given receptor and the compound to be tested for binding to this receptor is investigated.

As an example the cyanoenamines may be screened for the potassium channel opening acitivity. This can be achieved by first treating rat aorta with $^{86}Rb^+$, and then with the cyanoenamines I. The ratio of radioactive $^{86}Rb^+$ released into the solution and the radioactivity remaining in the tissue may be proportional to the potassium channel opening activity of the tested cyanoenamine I. This type of essay has been described in literature (see e.g. T. Nakajima, T. Izawa, T. Kashiwabara, S. Nakajima, Y. Munezuka, *Chem. Pharm. Bull.* 1994, 42, 2475–2490).

Cyanoenamines as I can also be prepared in solution. The method used is sketched below:

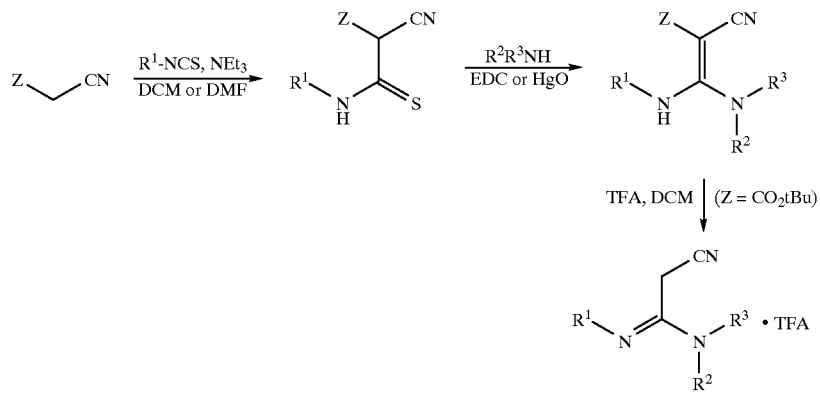

Acceptor substituted acetonitriles were reacted with isothiocyanates in the presence of a base. The resulting thioamides were treated with primary or secondary amines in the presence of a desulfurizing agent, as for instance mercury(II) oxide or EDC, to give cyanoenamines as I. Unsubstituted cyanoacetamidines could be prepared from cyanoenamines I with Z=tert-butyloxycarbonyl by treatment with trifluoroacetic acid in dichloromethane. Thereby hydrolysis of the estergroup, followed by decarboxylation occurs, to yield the corresponding cyanoacetamidine trifluoroacetates.

Prior Art

Some derivatives of 2-cyano-3-(dimethylamino)-3-arylamino-2-propenenitriles have been claimed to be angiotensin II antagonists (EP 591891, *Chem. Abstr.* 1995, 122, 81364; *Chem. Abstr.* 1994, 121, 300890). Example:

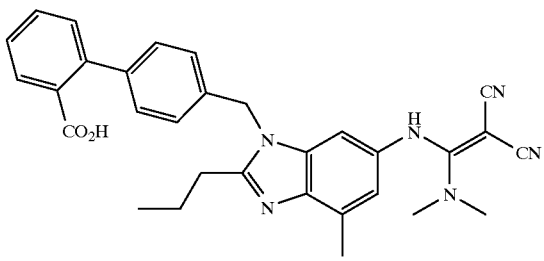

Other compounds containing this substructural element have been claimed to be antithrombotics (EP 547517, *Chem. Abstr.* 1993, 119, 249845; *Chem. Abstr.* 1993, 119, 180666), e.g.:

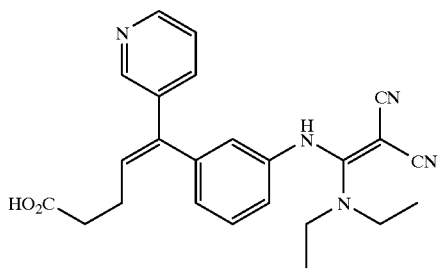

Several 3-(arylamino)-3-(alkylamino)-2-cyano-2-propenenitriles and -2-acrylamides have been claimed as fungicides and herbicides (EP 10396, *Chem. Abstr.* 1982, 97,140276; *Chem. Abstr.* 1980, 93, 144701), some examples being:

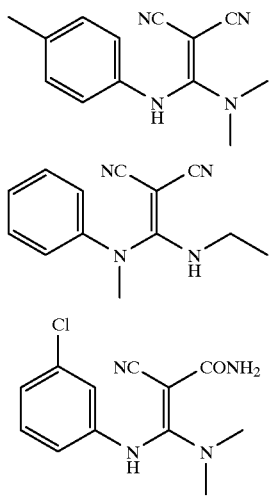

The reaction of amines RR'NH with mono-imidates of malononitrile of the general formula NC—CH$_2$—C(OR)=NH give compounds of the type RR'N—C(NH$_2$)=CH—CN, where one of the two amino groups is limited to be NH$_2$ (Cocco, M. T.; Congiu, C.; Maccioni, A.; Plumitallo, A., *J. Heterocycl. Chem.*, 1989, 26, 1859–1862; Klemm, K.; Pruesse, W.; Baron, L.; Daltrozzo, E., *Chem. Ber.*, 1981, 114, 2001–2018; Cocco, M. T.; Onnis, V., *Synthesis*, 1993, 2, 199–201; Fanshawe, W. J. et al., *J. Org. Chem.*, 1964, 29, 308–311; Troschuetz, R.; Dennstedt, T., *Arch. Pharm. (Weinheim Ger.)*, 1994, 327, 85–90).

A further method consists in the reaction of O-alkylated cyanoacetamides with aliphatic amines (G. J. Durant et al., patent, CH 606026, *Chem. Abstr.* 1979, 90, 87449, G. J. Durant, patent, U.S. Pat No. 4,024,260, *Chem. Abstr.*, 1977, 87, 135327). Also the reaction of 3,3-dimethoxyacrylonitrile with amines, which can be carried out stepwise in order to prepare compounds of the general formula RR'N—C(NR"R"')=CH—CN, has been reported (G. J. Durant, patent, U.S. Pat. No. 4,277,485, *Chem. Abstr.*, 1981, 95, 156591) and used for the preparation of ranitidine-analogues.

Moreover, the reaction of 3,3-dichloroacrylonitrile with amines has been reported to give cyanoenamines of the general structure (RR'N)$_2$C=CH—CN, with two identical amine-moieties RR'N— (Hashimoto et al., *J. Org. Chem.*, 1970, 35, 828–831; Takeda Chem.Ind.Ltd., JP 7022328, 1970, *Chem.Abstr.*, 73, 98434z). In addition to these, some special methods for the synthesis of these compounds have been described (e.g. Sasaki, T.; Kojima, A. *J. Chem. Soc. Sec. C,* 1970, 476–480; Clark, J., Parvizi, B., Southon, I. W., *J. Chem. Soc., Perkin Trans.* 1, 1976, 125–130; Smith; Kline and French Lab. Lim, FR 2229417, DE 2423813, Chem. Abstr., 82, 170943; Meyer; K., *Justus Liebigs Ann. Chem.*, 1978, 1491; Elagamey, A. G. A.; El-Taweel, F. M. A., *J. Prakt. Chem.*, 1991, 333, 333–338).

For the preparation of 2-acceptor-substituted 3,3-bis(alkyl/arylamino)-2-propenenitriles, several different synthetic methods have been described (Elvidge, J. A. et al., *J. Chem. Soc., Perkin Trans. I,* 1983, 1741–1744; Yatsishin, A. A., et al., *Zh. Org. Khim.* 1979, 15, 1381–1384; Hartke, K., *Angew. Chem.* 1964, 76, 781)

References

1. Gallop, M. A.; Barrett, R. W.; Dower, W. J.; Fodor, S. P. A.; Gordon, E. M. *J. Med. Chem.* 1994, 37, 1233–1251.
2. Gordon, E. M.; Barrett, R. W.; Dower, W. J.; Fodor, S. P. A.; Gallop, M. A. *J. Med. Chem.* 1994, 37, 1385–1401.
3. Terrett, N. K.; Gardner, M.; Gordon, D. W.; Kobylecki, R. J.; Steele, *J. Tetrahedron.* 1995, 51, 8135–8173.
4. Lebl, M.; Krchnák, V.; Sepetov, N. F.; Kocis, P.; Patek, M.; Flegelova, Z.; Ferguson, R.; Lam, K. S. *Journal Of Protein Chemistry.* 1994, 13, 484–486.
5. Sepetov, N. F.; Krchnák, V.; Stankova, M.; Wade, S.; Lam, K. S.; Lebl, M. *Proc. Natl. Acad. Sci. USA* 1995, 92, 5426–5430.
6. Liskamp, R. M. J. *Angew. Chem. Int. Ed. Engl.* 1994, 33, 633–636.
7. Houghten, R. A.; Kay, B. K.; Madden, D.; Krchnák, V.; Lebl, M.; Chabala, J. C.; Kauffman, S. *Perspectives in Drug Discovery and Design* 1994, 2, 249–325.
8. Seligmann, B.; Abdul-Latif, F.; Al-Obeidi, F.; Flegelova, Z. *European Journal Of Medicinal Chemistry* 1995, 30, 319–335.
9. Baldwin, J. J.; Burbaum, J. J.; Henderson, I.; Ohlmeyer, M. H. J. *J. Am. Chem. Soc.* 1995, 117, 5588–5589.
10. Jung et al., "Multiple Peptide Synthesis Methods and their Applications", *Angew. Chem. Int. Ed. Engl.* 1992, 31, 367–383.
11. J. A. Ellman, Solid phase and combinatorial synthesis of benzodiazepine compounds on a solid support, U.S. Pat. No. 5,288,514; Feb. 22, 1994.

Paharmacological Methods

The ability of the compounds to interact with potassium channels can be determined by various methods. When patch-clamp techniques (Hamill O. P., Marty A., Nefer E., Sakman B. and Sigworth F. J., *Plügers Arch.* 1981, 391, 85–100) are used the ionic current through a single channel of a cell can be recorded.

The activity of the compounds as potassium channel openers can also be measured as relaxation of rat aortas rings according to the following procedure:

A section of rat thoracic aorta between the aortic arch and the diaphragm was dissected out and mounted as ring preparations as described by Taylor P. D. et al. , *Brit. J. Pharmacol.*, 1994, 111, 42–48.

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

In the pancreatic b-cell the opening of the $K_{ATP}$-channels can be determined by measuring the subsequent change in the concentration of cytoplasmic free $Ca^{2+}$ concentration according to the method of Arkhammer P. et al., *J. Biol. Chem.* 1987, 262, 5448–5454.

$^{86}Rb^+$ efflux from a β-cell line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/mL $^{86}Rb^+$ and replated into microtiter plates (96 well cluster 3596, sterile, from Costar Corporation, MA, USA) at a density of 50000 cells/well in 100 µl/well, and grown 24 hours before use in assay.

The plates were washed 4 times with Ringer buffer (150 mM NaCl, 10 mM Hepes, 3.0 mM KCl, 1.0 mM $CaCl_2$, 20 mM sucrose, pH 7.1). Eighty µL Ringer buffer and 1 µL control- or test compound dissolved in DMSO was added. After incubation 1 h at room temperature with a lid, 50 µL of the supernatant was transferred to PicoPlates (Packard Instrument Company, CT, USA) and 100 µL MicroScint40 (Packard Instrument Company, CT, USA) added. The plates were counted in TopCount (Packard Instrument Company, CT, USA) for 1 min/well at the $^{32}P$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}=c$ and $E_{max}=d$, when the curve is turned of at infinite concentrations.

The compounds according to the invention are effective over a wide dosage range. In general satisfactory results are obtained with dosages from about 0.05 mg to about 1000 mg, preferably from about 0.1 mg to about 500 mg, per day. A most preferable dosage is about 5 mg to about 200 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| *Magnesii stearas* | 0.25 mg Ph. Eur. |

Due to their high degree of activity, the compounds of the invention may be administered to a mammal, especially a human, in need of such treatment, prevention, elimination, alleviation or amelioration of various diseases as mentioned above and especially of diseases of the endocrinological system such as hyperinsulinemia and diabetes. Such mammals include also animals, both domestic animals, e.g. household pets, and non-domestic animals such as wildlife.

EXAMPLES

Example 1

Synthesis of N-(4-methoxybenzyl)-N'-phenylcyanoacetamidine trifluoroacetate

To a suspension of Wang resin (20.0 g, 19.2 mmol, Novabiochem, loading: 0.96 mmol/g) in DCM (100 mL)

cyanoacetic acid (30.0 g, 353 mmol) and DMF (100 mL) were added. While stirring DIC (25 mL) was portionwise added, whereby an exothermic reaction took place. When the addition of DIC was completed, 4-dimethylaminopyridine (10 mL of a 1M solution in DMF) was added, and the resulting mixture stirred at room temperature for 15 h. The mixture was then filtered and the resin was washed extensively with DMF, DCM and methanol. After drying, approx. 20 g of Wang resin-O—CO—CH$_2$—CN was obtained.

To this resin (0.30 g, approx. 0.3 mmol, swollen in DCM) DMF (4 mL), diisopropylethylamine (0.8 mL) and phenylisothiocyanate (0.54 mL, 4.5 mmol) were added. The resulting mixture was shaken for 16 h, filtered, washed with DMF (3×6 mL) and a mixture of EDC (0.95 g, 4.95 mmol), DMF (5 mL) and 4-methoxybenzylamine (0.40 mL, 3.03 mmol) was then added. The mixture was shaken for 24 h, filtered, and the resin was carefully washed with DMF, methanol, DCM and 10% AcOH in DCM. It was then suspended in DCM (3 mL) and TFA (2 mL) and shaken for 35 min. Tetrachlorocarbon (5 mL) was the added, and after filtration and washing with DCM the filtrates were concentrated. Thereby 84 mg (71%) of N-(4-methoxybenzyl)-N'-phenylcyanoacetamidine trifluoroacetate were obtained as an oil, which slowly crystallized at room temperature within 48 h. Recrystallization (ethyl acetate/methanol/heptane) yielded 22 mg of the title compound as colourless crystals, mp 161–163° C.

LCMS (Lichrosorb RP 18, acetonitrile/water gradient, monitored at 214 nm): elution at 7.2 min; MH$^+$ calcd.: 280, found: 280. $^1$H NMR (300 MHz, CDCl$_3$/DMSO-d$_6$1:1) δ3.82 (s, br, 3H), 3.89 (s, br, 2H, exchangeable with D$_2$O), 4.60 (s, br, 2H), 6.95 (d, J=8.0 Hz, 2H), 7.29 (d, J=8.0 Hz, 2H), 7.30–7.55 (m, 5H), 10.25 (s, br, 1H); $^{13}$C NMR (75 MHz, DMSO-d$_6$) δ20.26 (t), 46.17 (t), 55.10 (q), 113.98 (d), 125.66 (d), 126.71 (d), 127.62 (d), 129.19 (d), 137.50 (s, br), 154.36 (s, br), 159.29 (s). Anal. Calcd. for C$_{19}$H$_{18}$F$_3$N$_3$O$_3$ (393.36): C, 58.01; H, 4.61; N, 10.68. Found: C, 57.98; H, 4.68; N, 10.47.

Example 2

Synthesis of 2-cyano-3-(3-methylbutylamino)-3-(phenylamino)-2-propenenitrile

To a solution of malononitrile (0.34 g, 5.15 mmol) in DMF (5 mL) at 0° C. first phenylisothiocyanate (0.60 mL, 5.02 mmol) and then triethylamine (1.4 mL) were added. The resulting mixture was stirred at 0° C. for 25 min, and then a freshly prepared mixture of EDC (2.90 g, 15.1 mmol), 3-methylbutylamine (1.20 mL, 10.3 mmol) and DMF (10 mL) was added. After stirring at room temperature for 2 d the mixture was poured into a mixture of ice-water (50 mL) and conc. HCl (3.0 mL). The product was extracted (2×30 mL ethyl acetate), the combined organic extracts were washed (2×30 mL brine), dried (magnesium sulfate) and concentrated. The remaining oil was mixed with methanol (3 mL), whereby a solid precipitated. After 20 h the solid was filtered off and dried in vacuo. 0.60 g (47%) of the title compound was obtained as slightly yellow crystals. Recrystallization from ethyl acetate/heptane yielded 0.40 g of an analytically pure sample, mp. 183–185° C. LCMS: MH$^+$ calcd.: 255, found: 255. $^1$H NMR (400 MHz, DMSO-d$_6$): δ=0.83 (d, J=7 Hz, 6H), 1.40 (q, J=7 Hz, 2H), 1.57 (nonett, J=7 Hz, 1H), 3.18 (m, 2H), 7.10 (m, 3H), 7.33 (t, J=8 Hz, 2H), 7,87 (s, br, 1H), 9.33 (s, 1H); $^{13}$C NMR (100 MHz, DMSO-d$_6$): δ=22.06, 24.90, 35.34, 37.38, 41.92, 118.11, 121.46, 124.16, 129.15, 138.81, 161.43. Anal. Calcd. for C$_{15}$H$_{18}$N$_4$ (254.34): C, 70.84; H, 7.13; N, 22.03. Found: C, 70.88; H, 7.28; N, 21.90.

Example 3

Synthesis of 3-[3,5-bis(trifluoromethyl) phenylamino]-2-cyano-3-(3-methylbutylamino) acrylic acid tert-butyl ester To a solution of 2-{N-[3,5-bis(trifluoromethyl)phenyl]thiocarbamoyl}cyanoacetic acid tert-butylester (1.12 g, 2.7 mmol, prepared from cyanoacetic acid tert-butyl ester and 3,5-bis(trifluoromethyl)phenylisothiocyanate) in DCM (15 mL) 3-methylbutylamine (1.0 mL, 8.60 mmol), magnesium sulfate (0.5 g) and mercury(II) oxide (2.0 g) were added. The resulting mixture was stirred at room temperature for 14 h, diluted with DCM (30 mL), filtered over Celite, washed with ice-cold diluted hydrochloric acid, with brine (2×20 mL), dried (magnesium sulfate) and concentrated. The residue was crystallized from heptane. 0.29 g (23%) of the title compound was obtained as colourless crystals, mp. 128–129° C. From the mother liquor additional 0.25 g (20%) of product were obtained. $^1$H NMR (400 MHz, DMSO-d$_6$): δ=0.82 (d, J=7 Hz, 6H), 1.41 (s, 9H), 1.43 (q, J=7 Hz, 2H), 1.57 (nonett, J=7 Hz, 1H), 3.18 (q, br, J=7 Hz, 2H), 7.63 (s, 2H), 7.70 (s, 1H), 8.91 (s, br, 1H), 9.52 (s, 1H); $^{13}$C NMR (100 MHz, DMSO-d$_6$): δ=21.96, 24.95, 28.02, 37.50, 41.84, 61.55, 79.66, 115.53, 118.67, 119.87, 123.05 (q, J=282 Hz), 130.44 (q, J=33 Hz), 142,11, 160.46, 167.93. Anal. Calcd. for C$_{21}$H$_{25}$F$_6$N$_3$O$_2$ (465.44): C, 54.19; H, 5.41; N, 9.03. Found: C, 54.27; H, 5.57; N, 8.84.

Example 4

Synthesis of 3-[3,5-bis(trifluoromethyl) phenylamino]-3-(3-methylbutylamino)-2-propenenitrile To a solution of 3-[3,5-bis(trifluoromethyl)phenylamino]-2-cyano-3-(3-methylbutylamino)acrylic acid tert-butyl ester (194 mg, 0.417 mmol) in DCM (2 mL) trifluoroacetic acid (2 mL) was added. After 30 min at room temperature the solution was concentrated, the residue was redissolved in carbon tetrachloride (10 mL) and reconcentrated. The product was purified by flash chromatography (6 g silica gel, gradient of heptane/ethyl acetate). 45 mg (30%) of the title compound was obtained as an oil. LCMS: MH$^+$=366. This compound was identical by LCMS to the product obtained from solid-phase synthesis.

Example 5

Synthesis of 3-[3,5-bis(trifluoromethyl) phenylamino]-2-cyano-3-(3-methylbutylamino)-2-propenenitrile To a solution of malononitrile (0.33 g, 5.00 mmol) in DCM at 0° C. first 3,5-bis(trifluoromethyl) phenylisothiocyanate (1.41 g, 5.20 mmol) and then triethylamine (1.0 mL) were added. The mixture was stirred at room temperature for 1 h 45 min and then DCM (5 mL), 3-methylbutylamine (1.0 mL, 8.60 mmol), magnesium sulfate (0.57 g) and mercury(II) oxide (2.54 g, 11.7 mmol) were added. The resulting mixture was stirred at room temperature for 17 h, whereby it turned black. This mixture was then filtrated (Celite), diluted with DCM (60 mL), washed with an ice-cold mixture of water (100 mL) and conc. HCl (2.0 mL), with brine (3×50 mL), dried (magnesium sulfate) and concentrated. The residue was purified by column chromatography (50 g silica gel, heptane/ethyl acetate gradient), to yield 1.22 g (63%) of the title compound as a foam. This foam could be crystallized from toluene/heptane, yielding 1.08 g of almost colourless crystals, mp. 158–159° C. $^1$H NMR (300 MHz, DMSO-d$_6$): δ=0.87 (d, J=7 Hz, 6H), 1.45 (q, J=7 Hz, 2H), 1.60 (nonett, J=7 Hz, 1H), 3.31 (m, 2H), 7.72 (s, 2H), 7.78 (s, 1H), 8.22 (s, br, 1H), 9.79 (s, 1H); $^{13}$C NMR (75 MHz, DMSO-d$_6$): δ=22.04, 24.99, 36.85, 37.14, 59.66, 116.52, 117.52, 121.21, 123.02 (q, J=275 Hz), 131.02 (q, J=33 Hz), 141,35, 161.27. Anal. Calcd. for C$_{17}$H$_{16}$F$_6$N$_4$ (390.33): C, 52.31; H, 4.13; N, 14.35. Found: C, 52.80; H, 4.29; N, 13.83.

Example 6

Synthesis of 3-[3,5-bis(trifluoromethyl) phenylamino]-3-(3-methylbutylamino)-2-(4-chlorophenylsulfonyl)-2-propenenitrile To a solution of 3,5-bis(trifluoromethyl) phenylisothiocyanate (1,44 g, 5.31 mmol) in DCM (15 mL) and acetonitrile (5 mL) first 4-chlorophenylsulfonylacetonitrile (1.10 g, 5.10 mmol) and then triethylamine (1.0 mL) were added. The resulting mixture was stirred at room temperature for 2 h 15 min, and then isoamylamine (0.65 mL, 5.59 mmol), mercury(II) oxide (2.70 g, 12.47 mmol) and magnesium sulfate (0.8 g) were added. Stirring was continued for 2 d. The mixture was then filtered, poured into a mixture of ice-water (200 mL) and concentrated hydrochloric acid (2 mL), phases were separated, the aqueous layer was extracted twice with DCM (20 mL) and the combined extracts were dried (magnesium sulfate) and concentrated. Column chromatography of the residue (100 g silica gel, gradient elution with heptane/ethyl acetate 10:0 to 3:1) gave 317 mg (12%) of the title compound as an oil. $^1$H NMR (300 MHz, DMSO-d$_6$): δ=0.79 (d, J=7 Hz, 6H), 1.39 (q, J=7 Hz, 2H), 1.50 (nonett, J=7 Hz, 1H), 3.31 (m, 2H), 7.27 (s, 2H), 7.67–7.80 (m, 5H), 8.13 (s, br, 1H), 9.76 (s, 1H); LCMS: elution at 16.23 min, MH$^+$: 540.

Example 7

Synthesis of 3-[3,5-bis(trifluoromethyl) phenylamino]-2-cyano-3-[3-(2-oxoazepan-1-yl) propylamino]acrylic acid tert-butyl ester To a mixture of 3,5-bis(trifluoromethyl) phenylisothiocyanate (2.83 g, 10.4 mmol), DCM (20 mL) and tert-butyl cyanoacetate (1.65 mL, 11.6 mmol) DBU (4.0 mL, 26.8 mmol) was added, whereby an exothermic reaction occurred. The resulting mixture was stirred at room temperature for 2 h, and then magnesium sulfate (2.0 g), isoamylamine (2.35 mL) and mercury(II) oxide (6.80 g, 31.4 mmol) were added. After stirring for 25 h, the mixture was mixed with celite, filtered, and the filtrate was mixed with 0.5 M hydrochloric acid. After an additional filtration the filtrate was extracted (3×100 mL DCM), the combined extracts were washed with brine (2×300 mL, emulgates strongly), dried (magnesium sulfate) and concentrated. Column chromatography (80 g silica gel, gradient elution with heptane/ethyl acetate 10:0 to 2:3) gave 2.23 g (39%) of the title compound as a colourless solid, along with 0.72 g (15%) of 3-[3,5-bis(trifluoromethyl)phenylamino]-2-cyano-3-(3-methylbutylamino)acrylic acid tert-butyl ester. A sample of the title compound was further purified by recrystallization. Colourless solid, mp. 167–168° C. (ethyl acetate). LCMS: elution at 15.4 min, MH$^+$: 549; $^1$H NMR (400 MHz, DMSO-d$_6$): δ=1.40 (s, 9H), 1.43 (m, 4H), 1.57 (m, 2H), 1.71 (q, J=7 Hz, 2H), 2.35 (m, 2H), 3.20 (q, J=7 Hz, 2H), 3.31 (m, 2H), 7.66 (s, 2H), 7.68 (s, 1H), 8.95 (s, br, 1H), 9.52 (s, 1H); $^{13}$C NMR (100 MHz, DMSO-d$_6$): δ=22.93, 27.93, 28.11, 28.32, 29.23, 36.44, 41.55, 44.47, 48.38, 61.93, 79.66, 115.36, 118.75, 119.89, 123.18 (q, J=275 Hz), 131.02 (q, J=33 Hz), 142.33, 160.59, 167.95, 174.74. Anal. Calcd. for C$_{25}$H$_{30}$F$_6$N$_4$O$_3$ (548.53): C, 54.74; H, 5.51; N, 10.21. Found: C, 54.62; H, 5.66; N, 9.97.

Example 8

Synthesis of 3-[3,5-bis(trifluoromethyl) phenylamino]-3-[3-(2-oxoazepan-1-yl)propylamino] acrylonitrile To a solution of 3-[3,5-bis(trifluoromethyl)phenylamino]-2-cyano-3-[3-(2-oxoazepan-1-yl)propylamino]acrylic acid tert-butyl ester (203 mg, 0.37 mmol) in DCM (6.0 mL) at 0° C. TFA (6.0 mL) was added. The resulting mixture was stirred at 0° C. for 30 min and then poured into an ice-cold, aqueous, saturated NaHCO$_3$-solution (100 mL). After dilution with DCM (30 mL) phases were separated, the aqueous layer was extracted (3×20 mL DCM), the combined extracts were washed with brine (2×50 mL), dried (magnesium sulfate) and concentrated, to yield 190 mg (100%) of the title compound as an oil (mixture of isomers). LCMS: elution at 9.97 min, MH$^+$: 449). $^1$H NMR (300 MHz, DMSO-d$_6$): δ=1.45–1.80 (m, 8H), 2.40 (m, 2H), 2.95 (m, 1H), 3.21 (m, 2H), 3.35 (m, 6H), 3.58 (s, br, 1H), 7.35–7.70 (m, 3H).

Example 9

Synthesis of 2-cyano-3-(4-methoxybenzylamino)-3-(phenylamino)acrylic acid tert-butyl ester To a solution of text-butyl cyanoacetate (1.3 mL, 9.12 mmol) in DMF (10 mL) at 0° C. first phenylisothiocyanate (1.2 mL, 10.0 mmol) and then triethylamine (2.80 mL) were added. The resulting mixture was stirred at 0° C. for 30 min and at room temperature for 30 min. The mixture was then cooled down to 0° C. and EDC (5.77 g, 30.1 mmol), DMF (30 mL) and 4-methoxybenzylamine (2.65 mL, 20.3 mmol) were added. After stirring for 9 h at room temperature, for 14 h at 60° C. and then for 2d at room temperature, the mixture was poured on ice (150 ml) and conc. HCl (4 mL). Extraction (3×30 mL ethyl acetate), drying of the combined extracts (magnesium sulfate) and concentration yields an oil, which is purified by column chromatography (50 g silica gel, gradient elution with heptane/ethyl acetate 1:0 to 1:4). 0.43 g (12%) of the title compound are obtained as a colourless solid, mp. 158–159° C. (ethyl acetate/heptane). $^1$H NMR (400 MHz, DMSO-d$_6$): δ=1.39 (s, 9H), 3.72 (s, 3H), 4.22 (s, br, 2H), 6.89 (d, J=8 Hz, 2H), 7.02–7.16 (m, 5H), 7.32 (m, 2H), 8.95 (s, br, 0.5H), 9.18 (s, 0.5H). Anal. Calcd. for C$_{22}$H$_{25}$N$_3$O$_3$ (379.46): C, 69.64; H, 6.64; N, 11.07. Found: C, 69.51; H, 6.80; N, 10.89.

Example 10

Automated Synthesis of an Array of Eighty Different Cyanoenamines

An array of eighty different cyanoenamines has been prepared in the following way: Into eighty reactors of the multiple organic synthesizer "ACT 496" of "Advanced ChemTech" 100 mg of Wang-resin-bound cyanoacetic acid (prepared as described in example 1) was equally distributed. Then each of the eighty reactors was treated as described in example 1 with one of 8 different aromatic isothiocyanates, namely 4-trifluoromethylphenylisothiocyanate, 2-trifluoromethylphenylisothiocyanate, 2,3-dichlorophenylisothiocyanate, 3-chloro-4-fluorophenylisothiocyanate, 2-methoxy-4-nitrophenylisothiocyanate, 2,4-difluorophenylisothiocyanate, 4-cyanophenylisothiocyanate and 3,5-bis(trifluoromethyl)phenylisothiocyanate. The resulting thioamides were then treated with ten different primary amines, namely with 2-methylpropylamine, 1,2-dimethylpropylamine, isopropylamine, 1,3-dimethylbutylamine, 2,2-dimethylpropylamine, butylamine, 4-tert-butylcyclohexylamine, 1,2,2-trimethylpropylamine, exo-2-norbornylamine and cyclohexylmethylamine in such a way, that all possible combinations of isothiocyanateamine were realized. After extensive washing, the resulting resin-bound cyanoenamines were cleaved from the substrate by treatment with 50% TFA in DCM (30 min), yielding an array of eighty different cyanoenamines in purities of 70–>90% (HPLC). The samples were redissolved several times in methanol and concentrated again in order to remove traces of TFA. Finally the samples were redissolved in methanol (2 mL) and triethylamine (0.05 mL), concentrated again and redissolved in DMSO (3.5 mL). The resulting solutions were used for the screening.

Following the procedure given above, the following cyanoenamine derivatives I have been prepared:

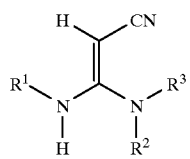

I

| No | $R^1$ | —$NR^2R^3$ | $MH^+$ expctd | found |
|---|---|---|---|---|
| 1 | 4-(trifluoromethyl)phenyl | 2-(methylpropyl)amino | | |
| 2 | 4-(trifluoromethyl)phenyl | (1,2-dimethylpropyl)amino | | |
| 3 | 4-(tri.fluoromethyl)phenyl | isopropylamino | | |
| 4 | 4-(trifluoromethyl)phenyl | (1,3-dimethylbutyl)amino | | |
| 5 | 4-(trifluoromethyl)phenyl | (2,2-dimethylpropyl)amino | | |
| 6 | 4-(trifluoromethyl)phenyl | butylamino | | |
| 7 | 4-(trifluoromethyl)phenyl | (4-tert-butylcyclohexyl)amino | 366 | 366 |
| 8 | 4-(trifluoromethyl)phenyl | (1,2,2-trimethylpropyl)amino | | |
| 9 | 4-(trifluoromethyl)phenyl | 2-exo-norbornylamino | | |
| 10 | 4-(trifluoromethyl)phenyl | (cyclohexylmethyl)amino | | |
| 11 | 2-(trifluoromethyl)phenyl | 2-(methylpropyl)amino | | |
| 12 | 2-(trifluoromethyl)phenyl | (1,2-dimethylpropyl)amino | | |
| 13 | 2-(trifluoromethyl)phenyl | isopropylamino | | |
| 14 | 2-(trifluoromethyl)phenyl | (1,3-dimethylbutyl)amino | | |
| 15 | 2-(trifluoromethyl)phenyl | (2,2-dimethylpropyl)amino | | |
| 16 | 2-(trifluoromethyl)phenyl | butylamino | 284 | 284 |
| 17 | 2-(trifluoromethyl)phenyl | (4-tert-butylcyclohexyl)amino | | |
| 18 | 2-(trifluoromethyl)phenyl | (1,2,2-trimethylpropyl)amino | | |
| 19 | 2-(trifluoromethyl)phenyl | 2-exo-norbornylamino | | |
| 20 | 2-(trifluoromethyl)phenyl | (cyclohexylmethyl)amino | | |
| 21 | 2,3-dichlorophenyl | 2-(methylpropyl)amino | | |
| 22 | 2,3-dichlorophenyl | (1,2-dimethylpropyl)amino | | |
| 23 | 2,3-dichlorophenyl | isopropylamino | | |
| 24 | 2,3-dichlorophenyl | (1,3-dimethylbutyl)amino | | |
| 25 | 2,3-dichlorophenyl | (2,2-dimethylpropyl)amino | 298 | 298 |
| 26 | 2,3-dichlorophenyl | butylamino | | |
| 27 | 2,3-dichlorophenyl | (4-tert-butylcyclohexyl)amino | | |
| 28 | 2,3-dichlorophenyl | (1,2,2-trimethylpropyl)amino | | |
| 29 | 2,3-dichlorophenyl | 2-exo-norbornylamino | | |
| 30 | 2,3-dichlorophenyl | (cyclohexylmethyl)amino | | |
| 31 | 2-methoxy-4-nitrophenyl | 2-(methylpropyl)amino | 291 | 291 |
| 32 | 2-methoxy-4-nitrophenyl | (1,2-dimethylpropyl)amino | | |
| 33 | 2-methoxy-4-nitrophenyl | isopropylamino | | |
| 34 | 2-methoxy-4-nitrophenyl | (1,3-dimethylbutyl)amino | | |
| 35 | 2-methoxy-4-nitrophenyl | (2,2-dimethylpropyl)amino | | |
| 36 | 2-methoxy-4-nitrophenyl | butylamino | | |
| 37 | 2-methoxy-4-nitrophenyl | (4-tert-butylcyclohexyl)amino | | |
| 38 | 2-methoxy-4-nitrophenyl | (1,2,2-trimethylpropyl)amino | | |
| 39 | 2-methoxy-4-nitrophenyl | 2-exo-norbornylamino | | |
| 40 | 2-methoxy-4-nitrophenyl | (cyclohexylmethyl)amino | 331 | 331 |
| 41 | 2,4-difluorophenyl | 2-(methylpropyl)amino | | |
| 42 | 2,4-difluorophenyl | (1,2-dimethylpropyl)amino | 266 | 266 |
| 43 | 2,4-difluorophenyl | isopropylamino | | |
| 44 | 2,4-difluorophenyl | (1,3-dimethylbutyl)amino | | |
| 45 | 2,4-difluorophenyl | (2,2-dimethylpropyl)amino | | |
| 46 | 2,4-difluorophenyl | butylamino | | |
| 47 | 2,4-difluorophenyl | (4-tert-butylcyclohexyl)amino | | |
| 48 | 2,4-difluorophenyl | (1,2,2-trimethylpropyl)amino | | |
| 49 | 2,4-difluorophenyl | 2-exo-norbornylamino | | |

-continued

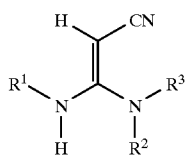

I

| No | R¹ | —NR²R³ | MH⁺ expctd | found |
|---|---|---|---|---|
| 50 | 2,4-difluorophenyl | (cyclohexylmethyl)amino | | |
| 51 | 3-chloro-4-fluorophenyl | 2-(methylpropyl)amino | | |
| 52 | 3-chloro-4-fluorophenyl | (1,2-dimethylpropyl)amino | 282 | 282 |
| 53 | 3-chloro-4-fluorophenyl | isopropylamino | | |
| 54 | 3-chloro-4-fluorophenyl | (1,3-dimethylbutyl)amino | | |
| 55 | 3-chloro-4-fluorophenyl | (2,2-dimethylpropyl)amino | | |
| 56 | 3-chloro-4-fluorophenyl | butylamino | | |
| 57 | 3-chloro-4-fluorophenyl | (4-tert-butylcyclohexyl)amino | 350 | 350 |
| 58 | 3-chloro-4-fluorophenyl | (1,2,2-trimethylpropyl)amino | | |
| 59 | 3-chloro-4-fluorophenyl | 2-exo-norbornylamino | | |
| 60 | 3-chloro-4-fluorophenyl | (cyclohexylmethyl)amino | | |
| 61 | 4-cyanophenyl | 2-(methylpropyl)amino | | |
| 62 | 4-cyanophenyl | (1,2-dimethylpropyl)amino | 255 | 255 |
| 63 | 4-cyanophenyl | isopropylamino | | |
| 64 | 4-cyanophenyl | (1,3-dimethylbutyl)amino | | |
| 65 | 4-cyanophenyl | (2,2-dimethylpropyl)amino | | |
| 66 | 4-cyanophenyl | butylamino | | |
| 67 | 4-cyanophenyl | (4-tert-butylcyclohexyl)amino | | |
| 68 | 4-cyanophenyl | (1,2,2-trimethylpropyl)amino | | |
| 69 | 4-cyanophenyl | 2-exo-norbornylamino | | |
| 70 | 4-cyanophenyl | (cyclohexylmethyl)amino | | |
| 71 | 3,5-bis(trifluoromethyl)phenyl | 2-(methylpropyl)amino | 352 | 352 |
| 72 | 3,5-bis(trifluoromethyl)phenyl | (1,2-dimethylpropyl)amino | | |
| 73 | 3,5-bis(trifluoromethyl)phenyl | isopropylamino | 338 | 338 |
| 74 | 3,5-bis(trifluoromethyl)phenyl | (1,3-dimethylbutyl)amino | 380 | 380 |
| 75 | 3,5-bis(trifluoromethyl)phenyl | (2,2-dimethylpropyl)amino | 366 | 366 |
| 76 | 3,5-bis(trifluoromethyl)phenyl | butylamino | | |
| 77 | 3,5-bis(trifluoromethyl)phenyl | (4-tert-butylcyclohexyl)amino | 434 | 434 |
| 78 | 3,5-bis(trifluoromethyl)phenyl | (1,2,2-trimethylpropyl)amino | | |
| 79 | 3,5-bis(trifluoromethyl)phenyl | 2-exo-norbornylamino | 390 | 390 |
| 80 | 3,5-bis(trifluoromethyl)phenyl | (cyclohexylmethyl)amino | | |
| 81 | phenyl | (4-methoxybenzyl)amino | 280 | 280 |
| 82 | 3-fluorophenyl | propylamino | 220 | 220 |
| 83 | 3-fluorophenyl | hexylamino | 262 | 262 |
| 84 | 3-fluorophenyl | propargylamino | 216 | 216 |
| 85 | 3-fluorophenyl | (3-methylbutyl)amino | 248 | 248 |
| 86 | 3-pyridyl | propylamino | 203 | 203 |
| 87 | 3-pyridyl | hexylamino | 245 | 245 |
| 88 | 3-pyridyl | propargylamino | 199 | 199 |
| 89 | 3-pyridyl | (3-methylbutyl)amino | 231 | 231 |
| 90 | 314-dichlorophenyl | propylamino | 271 | 271 |
| 91 | 3,4-dichlorophenyl | hexylamino | 313 | 313 |
| 91 | 314-dichlorophenyl | propargylamino | 267 | 267 |
| 92 | 314-dichlorophenyl | (3-methylbutyl)amino | 299 | 299 |
| 94 | 3,5-bis(trifluoromethyl)phenyl | propylamino | 338 | 338 |
| 95 | 315-bis(trifluoromethyl)phenyl | hexylamino | 380 | 380 |
| 96 | 3,5-bis(trifluoromethyl)phenyl | propargylamino | 334 | 334 |
| 97 | 3,5-bis(trifluoromethyl)phenyl | (3-methylbutyl)amino | 366 | 366 |
| 98 | phenyl | phenylamino | 236 | 236 |
| 99 | benzyl | (4-methoxybenzyl)amino | 294 | 294 |
| 100 | phenyl | 1-pyrrolidinyl | 214 | 214 |
| 101 | 3-(trifluoromethyl)phenyl | (3-methylbutyl)amino | 297 | 297 |
| 102 | 4-chloro-3-(trifluoromethyl) | (3-methylbutyl)amino | 331 | 331 |

-continued

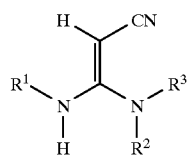

I

| No | R¹ | —NR²R³ | MH⁺ expctd | found |
|---|---|---|---|---|
| | phenyl | | | |
| 103 | 3-acetylphenyl | (3-methylbutyl)amino | 271 | 271 |
| 104 | 2-chloro-5-(trifluoromethyl)-phenyl | (3-methylbutyl)amino | 331 | 331 |
| 105 | 3,4-dicyanophenyl | (3-methylbutyl)amino | 279 | 279 |
| 106 | 4-bromo-2-(trifluoromethyl)-phenyl | (3-methylbutyl)amino | 376 | 376 |
| 107 | 4,6-dimethyl-2-pyrimidinyl | (3-methylbutyl)amino | 259 | 259 |
| 108 | 4-acetylphenyl | (3-methylbutyl)amino | 271 | 271 |
| 109 | 3,5-dichlorophenyl | (3-methylbutyl)amino | 298 | 298 |
| 110 | 3-chloro-4-methylphenyl | (3-methylbutyl)amino | 277 | 277 |
| 111 | 2,5-bis(trifluoromethyl)phenyl | (3-methylbutyl)amino | 366 | 366 |
| 112 | 3,5-dichlorophenyl | (2-methylpropyl)amino | 284 | 284 |
| 113 | 3-chloro-4-methylphenyl | (2-methylpropyl)amino | 263 | 263 |
| 114 | 2,5 bis(trifluoromethyl)phenyl | (2-methylpropyl)amino | 351 | 351 |
| 115 | 3,5-bis(trifluoromethyl)phenyl | (3-phenylpropyl)amino | 413 | 413 |
| 116 | 3,5-bis(trifluoromethyl)phenyl | (2,2,6,6-tetramethyl-4-piperidinyl)amino | 434 | 434 |
| 117 | 3,5-bis(trifluoromethyl)phenyl | N,N-dipropylamino | 379 | 379 |
| 118 | 3,5-bis(trifluoromethyl)phenyl | 2-(4-chlorophenyl)ethylamino | 433 | 433 |
| 119 | 3,5-bis(trifluoromethyl)phenyl | 2-(2-pyridyl)ethylamino | 400 | |
| 120 | 3,5-bis(trifluoromethyl)phenyl | 4-methyl-1-piperidyl | 377 | 377 |
| 121 | 3,5-bis(trifluoromethyl)phenyl | N,N-bis(2-methylpropyl)amino | 407 | 407 |
| 122 | 3,5-bis(trifluoromethyl)phenyl | 1-pyrrolidinyl | 349 | 349 |
| 123 | 3,5-bis(trifluoromethyl)phenyl | 3-(1-imidazolyl)propylamino | 403 | 403 |
| 124 | 3,5-bis(trifluoromethyl)phenyl | N-methyl-N-(3-pyridyl)methylamino | 400 | 400 |
| 125 | 3,5-bis(trifluoromethyl)phenyl | (3-amino-2,2-dimethylpropyl)amino | 380 | 380 |
| 126 | 3,5-bis(trifluoromethyl)phenyl | 3-(2-oxo-1-pyrrolidinyl)propylamino | 420 | 420 |
| 127 | 3,5-bis(trifluoromethyl)phenyl | (4-methoxybenzyl)amino | 415 | 415 |
| 128 | 3,5-bis(trifluoromethyl)phenyl | 3-hydroxy-1-piperidinyl | 379 | |
| 129 | 3,5-bis(trifluoromethyl)phenyl | tetrahydroisoquinolin-1-yl | 411 | 411 |
| 130 | 3,5-bis(trifluoromethyl)phenyl | 2,6-cis-dimethyl-4-morpholinyl | 393 | 393 |
| 131 | 3,5-bis(trifluoromethyl)phenyl | 4-[(3-trifluoromethyl)phenyl]-1-piperazinyl | 508 | 508 |
| 132 | 3,5-bis(trifluoromethyl)phenyl | 4-tert-butyl-1-piperidinyl | 419 | 419 |
| 133 | 3,5-bis(trifluoromethyl)phenyl | 1-azepanyl | 377 | 377 |
| 134 | 3,5-bis(trifluoromethyl)phenyl | 4-benzoyl-1-piperidinyl | 467 | 467 |
| 135 | phenyl | tetrahydroisoquinolin-1-yl | 275 | 275 |
| 136 | phenyl | (4-methylphenyl)amino | 249 | 249 |
| 137 | 3-cyanophenyl | 4-(4-chlorophenyl)-1-piperazinyl | 363 | 363 |
| 138 | 3-acetylphenyl | tetrahydroisoquinolin-1-yl | 317 | 317 |
| 139 | 3-cyanophenyl | N-ethyl-N-phenylamino | 289 | 289 |
| 140 | phenyl | (4-chlorophenyl)amino | 270 | 270 |

What is claimed is:
1. A compound of the general formula I

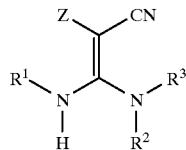

wherein
R¹ is alkyl optionally substituted with halogen, hydroxy, alkoxy, aryloxy, alkylthio, arylthio, dialkylamino, arylalkylamino or diarylamino; aralkyl, aryl optionally substituted with alkyl, trifluoromethyl, aryl, heteroaryl, halogen, alkoxy, aryloxy, dialkylamino, alkylarylamino, diarylamino, nitro, alkyl-sulfonyl, aryl-sulfonyl, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxycarbonyl or aminocarbonyl;

R² and R³ are independently hydrogen; alkyl optionally substituted with aryl, heteroaryl, a 5-,6- or 7-membered heterocyclic system, halogen, hydroxy, alkoxy, aryloxy, alkylthio, arylthio, dialkylamino, arylalkylamino or diarylamino; aryl optionally substituted with alkyl, aryl, heteroaryl, halogen, alkoxy, aryloxy, dialkylamino, alkylarylamino, diarylamino, nitro, alkyl-sulfonyl, aryl-sulfonyl, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxycarbonyl or aminocarbonyl;

or R² and R³ are linked together by $-(CH_2)_n-$, n being 4–7, provided that R² and R³ cannot be hydrogen at the same time;

Z is hydrogen, cyano, alkoxycarbonyl, optionally substituted aminocarbonyl, alkylsulfonyl or arylsulfonyl optionally substituted with alkyl, aryl, heteroaryl, halogen, alkoxy, aryloxy, dialkylamino, alkylarylamino, diarylamino, halogen, nitro, alkyl-sulfonyl, aryl-sulfonyl, cyano, alkoxycarbonyl or aminocarbonyl; and pharmaceutically acceptable salts thereof.

2. A compound according to claim 1 wherein R¹ is optionally substituted aryl.

3. A compound according to claim 2 wherein R¹ is optionally substituted phenyl.

4. A compound according to claim 3 wherein R¹ is phenyl substituted by one or two halogen-, perhalomethyl- or cyano-groups.

5. A compound according to claim 1 wherein Z is hydrogen.

6. A compound according to claim 1, wherein the compounds of formula I are selected from the group consisting of:

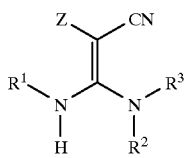

| No | R¹ | —NR²R³ | Z |
|---|---|---|---|
| 1 | 4-(trifluoromethyl)phenyl | 2-(methylpropyl)amino | H |
| 2 | 4-(trifluoromethyl)phenyl | (1,2-dimethylpropyl)amino | H |
| 3 | 4-(trifluoromethyl)phenyl | isopropylamino | H |
| 4 | 4-(trifluoromethyl)phenyl | (1,3-dimethylbutyl)amino | H |
| 5 | 4-(trifluoromethyl)phenyl | (2,2-dimethylpropyl)amino | H |
| 6 | 4-(trifluoromethyl)phenyl | butylamino | H |
| 7 | 4-(trifluoromethyl)phenyl | (4-tert-butylcyclohexyl)amino | H |
| 5 | 4-(trifluoromethyl)phenyl | (1,2,2-trimethylpropyl)amino | H |
| 9 | 4-(trifluoromethyl)phenyl | 2-exo-norbornylamino | H |
| 10 | 4-(trifluoromethyl)phenyl | (cyclohexylmethyl)amino | H |
| 11 | 2-(trifluoromethyl)phenyl | 2-(methylpropyl)amino | H |
| 12 | 2-(trifluoromethyl)phenyl | (1,2-dimethylpropyl)amino | H |
| 13 | 2-(trifluoromethyl)phenyl | isopropylamino | H |
| 14 | 2-(trifluoromethyl)phenyl | (1,3-dimethylbutyl)amino | H |
| 15 | 2-(trifluoromethyl)phenyl | (2,2-dimethylpropyl)amino | H |
| 16 | 2-(trifluoromethyl)phenyl | butylamino | H |
| 17 | 2-(trifluoromethyl)phenyl | (4-tert-butylcyclohexyl)amino | H |
| 18 | 2-(trifluoromethyl)phenyl | (1,2,2-trimethylpropyl)amino | H |
| 19 | 2-(trifluoromethyl)phenyl | 2-exo-norbornylamino | H |
| 20 | 2-(trifluoromethyl)phenyl | (cyclohexylmethyl)amino | H |
| 21 | 2,3-dichlorophenyl | 2-(methylpropyl)amino | H |
| 22 | 2,3-dichlorophenyl | (1,2-dimethylpropyl)amino | H |
| 23 | 2,3-dichlorophenyl | isopropylamino | H |
| 24 | 2,3-dichlorophenyl | (1,3-dimethylbutyl)amino | H |
| 25 | 2,3-dichlorophenyl | (2,2-dimethylpropyl)amino | H |
| 26 | 2,3-dichlorophenyl | butylamino | H |
| 27 | 2,3-dichlorophenyl | (4-tert-butylcyclohexyl)amino | H |
| 25 | 2,3-dichlorophenyl | (1,2,2-trimethylpropyl)amino | H |
| 29 | 2,3-dichlorophenyl | 2-exo-norbornylamino | H |

-continued

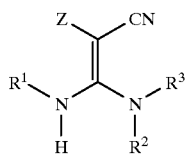

I

| No | R$^1$ | —NR$^2$R$^3$ | Z |
|----|-------|--------------|---|
| 30 | 2,3-dichlorophenyl | (cyclohexylmethyl)amino | H |
| 31 | 2-methoxy-4-nitrophenyl | 2-(methylpropyl)amino | H |
| 32 | 2-methoxy-4-nitrophenyl | (1,2-dimethylpropyl)amino | H |
| 33 | 2-methoxy-4-nitrophenyl | isopropylamino | H |
| 34 | 2-methoxy-4-nitrophenyl | (1,3-dimethylbutyl)amino | H |
| 35 | 2-methoxy-4-nitrophenyl | (2,2-dimethylpropyl)amino | H |
| 36 | 2-methoxy-4-nitrophenyl | butylamino | H |
| 37 | 2-methoxy-4-nitrophenyl | (4-tert-butylcyclohexyl)amino | H |
| 38 | 2-methoxy-4-nitrophenyl | (1,2,2-trimethylpropyl)amino | H |
| 39 | 2-methoxy-4-nitrophenyl | 2-exo-norbornylamino | H |
| 40 | 2-methoxy-4-nitrophenyl | (cyclohexylmethyl)amino | H |
| 41 | 2,4-difluorophenyl | 2-(methylpropyl)amino | H |
| 42 | 2,4-difluorophenyl | (1,2-dimethylpropyl)amino | H |
| 43 | 2,4-difluorophenyl | isopropylamino | H |
| 44 | 2,4-difluorophenyl | (1,3-dimethylbutyl)amino | H |
| 45 | 2,4-difluorophenyl | (2,2-dimethylpropyl)amino | H |
| 46 | 2,4-difluorophenyl | butylamino | H |
| 47 | 2,4-difluorophenyl | (4-tert-butylcyclohexyl)amino | H |
| 48 | 2,4-difluorophenyl | (1,2,2-trimethylpropyl)amino | H |
| 49 | 2,4-difluorophenyl | 2-exo-norbornylamino | H |
| 50 | 2,4-difluorophenyl | (cyclohexylmethyl)amino | H |
| 51 | 3-chloro-4-fluorophenyl | 2-(methylpropyl)amino | H |
| 52 | 3-chloro-4-fluorophenyl | (1,2-dimethylpropyl)amino | H |
| 53 | 3-chloro-4-fluorophenyl | isopropylamino | H |
| 54 | 3-chloro-4-fluorophenyl | (1,3-dimethylbutyl)amino | H |
| 55 | 3-chloro-4-fluorophenyl | (2,2-dimethylpropyl)amino | H |
| 56 | 3-chloro-4-fluorophenyl | butylamino | H |
| 57 | 3-chloro-4-fluorophenyl | (4-tert-butylcyclohexyl)amino | H |
| 58 | 3-chloro-4-fluorophenyl | (1,2,2-trimethylpropyl)amino | H |
| 59 | 3-chloro-4-fluorophenyl | 2-exo-norbornylamino | H |
| 60 | 3-chloro-4-fluorophenyl | (cyclohexylmethyl)amino | H |
| 61 | 4-cyanophenyl | 2-(methylpropyl)amino | H |
| 62 | 4-cyanophenyl | (1,2-dimethylpropyl)amino | H |
| 63 | 4-cyanophenyl | isopropylamino | H |
| 64 | 4-cyanophenyl | (1,3-dimethylbutyl)amino | H |
| 65 | 4-cyanophenyl | (2,2-dimethylpropyl)amino | H |
| 66 | 4-cyanophenyl | butylamino | H |
| 67 | 4-cyanophenyl | (4-tert-butylcyclohexyl)amino | H |
| 68 | 4-cyanophenyl | (1,2,2-trimethylpropyl)amino | H |
| 69 | 4-cyanophenyl | 2-exo-norbornylamino | H |
| 70 | 4-cyanophenyl | (cyclohexylmethyl)amino | H |
| 71 | 3,5-bis(trifluoromethyl)phenyl | 2-(methylpropyl)amino | H |
| 72 | 3,5-bis(trifluoromethyl)phenyl | (1,2-dimethylpropyl)amino | H |
| 73 | 3,5-bis(trifluoromethyl)phenyl | isopropylamino | H |
| 74 | 3,5-bis(trifluoromethyl)phenyl | (1,3-dimethylbutyl)amino | H |
| 75 | 3,5-bis(trifluoromethyl)phenyl | (2,2-dimethylpropyl)amino | H |
| 76 | 3,5-bis(trifluoromethyl)phenyl | butylamino | H |
| 77 | 3,5-bis(trifluoromethyl)phenyl | (4-tert-butylcyclohexyl)amino | H |
| 78 | 3,5-bis(trifluoromethyl)phenyl | (1,2,2-trimethylpropyl)amino | H |
| 79 | 3,5-bis(trifluoromethyl)phenyl | 2-exo-norbornylamino | H |
| 80 | 3,5-bis(trifluoromethyl)phenyl | (cyclohexylmethyl)amino | H |
| 81 | phenyl | (4-methoxybenzyl)amino | H |
| 82 | 3-fluorophenyl | propylamino | H |
| 83 | 3-fluorophenyl | hexylamino | H |
| 84 | 3-fluorophenyl | propargylamino | H |
| 85 | 3-fluorophenyl | (3-methylbutyl)amino | H |
| 86 | 3-pyridyl | propylamino | H |
| 87 | 3-pyridyl | hexylamino | H |

-continued

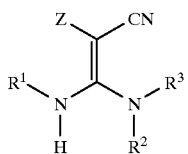

I

| No | R¹ | —NR²R³ | Z |
|---|---|---|---|
| 88 | 3-pyridyl | propargylamino | H |
| 89 | 3-pyridyl | (3-methylbutyl)amino | H |
| 90 | 3,4-dichlorophenyl | propylamino | H |
| 91 | 3,4-dichlorophenyl | hexylamino | H |
| 91 | 3,4-dichlorophenyl | propargylamino | H |
| 92 | 3,4-dichlorophenyl | (3-methylbutyl)amino | H |
| 94 | 3,5-bis(trifluoromethyl)phenyl | propylamino | H |
| 95 | 3,5-bis(trifluoromethyl)phenyl | hexylamino | H |
| 96 | 3,5-bis(trifluoromethyl)phenyl | propargylamino | H |
| 97 | 3,5-bis(trifluoromethyl)phenyl | (3-methylbutyl)amino | H |
| 98 | phenyl | phenylamino | H |
| 99 | benzyl | (4-methoxybenzyl)amino | H |
| 100 | phenyl | 1-pyrrolidinyl | H |
| 101 | 3-(trifluoromethyl)phenyl | (3-methylbutyl)amino | H |
| 102 | 4-chloro-3-(trifluoromethyl)-phenyl | (3-methylbutyl)amino | H |
| 103 | 3-acetylphenyl | (3-methylbutyl)amino | H |
| 104 | 2-chloro-5-(trifluoromethyl)-phenyl | (3-methylbutyl)amino | H |
| 105 | 3,4-dicyanophenyl | (3-methylbutyl)amino | H |
| 106 | 4-bromo-2-(trifluoromethyl)-phenyl | (3-methylbutyl)amino | H |
| 107 | 4,6-dimethyl-2-pyrimidinyl | (3-methylbutyl)amino | H |
| 108 | 4-acetylphenyl | (3-methylbutyl)amino | H |
| 109 | 3,5-dichlorophenyl | (3-methylbutyl)amino | H |
| 110 | 3-chloro-4-methylphenyl | (3-methylbutyl)amino | H |
| 111 | 2,5-bis(trifluoromethyl)phenyl | (3-methylbutyl)amino | H |
| 112 | 3,5-dichlorophenyl | (2-methylpropyl)amino | H |
| 113 | 3-chloro-4-methylphenyl | (2-methylpropyl)amino | H |
| 114 | 2,5-bis(trifluoromethyl)phenyl | (2-methylpropyl)amino | H |
| 115 | 3,5-bis(trifluoromethyl)phenyl | (3-phenylpropyl)amino | H |
| 116 | 3,5-bis(trifluoromethyl)phenyl | (2,2,6,6-tetramethyl-4-piperidinyl)amino | H |
| 117 | 3,5-bis(trifluoromethyl)phenyl | N,N-dipropylamino | H |
| 118 | 3,5-bis(trifluoromethyl)phenyl | 2-(4-chlorophenyl)ethylamino | H |
| 119 | 3,5-bis(trifluoromethyl)phenyl | 2-(2-pyridyl)ethylamino | H |
| 120 | 3,5-bis(trifluoromethyl)phenyl | 4-methyl-1-piperidyl | H |
| 121 | 3,5-bis(trifluoromethyl)phenyl | N,N-bis(2-methylpropyl)amino | H |
| 122 | 3,5-bis(trifluoromethyl)phenyl | 1-pyrrolidinyl | H |
| 123 | 3,5-bis(trifluoromethyl)phenyl | 3-(1-imidazolyl)propylamino | H |
| 124 | 3,5-bis(trifluoromethyl)phenyl | N-methyl-N-(3-pyridyl)methylamino | H |
| 125 | 3,5-bis(trifluoromethyl)phenyl | (3-amino-2,2-dimethylpropyl)amino | H |
| 126 | 3,5-bis(trifluoromethyl)phenyl | 3-(2-oxo-1-pyrrolidinyl)propylamino | H |
| 127 | 3,5-bis(trifluoromethyl)phenyl | (4-methoxybenzyl)amino | H |
| 128 | 3,5-bis(trifluoromethyl)phenyl | 3-hydroxy-1-piperidinyl | H |
| 129 | 3,5-bis(trifluoromethyl)phenyl | tetrahydroisoquinolin-1-yl | H |
| 130 | 3,5-bis(trifluoromethyl)phenyl | 2,6-cis-dimethyl-4-morpholinyl | H |

-continued

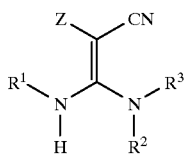

I

| No | R¹ | —NR²R³ | Z |
|---|---|---|---|
| 131 | 3,5-bis(trifluoromethyl)phenyl | 4-[(3-trifluoromethyl)phenyl]-1-piperazinyl | H |
| 132 | 3,5-bis(trifluoromethyl)phenyl | 4-tert-butyl-1-piperidinyl | H |
| 133 | 3,5-bis(trifluoromethyl)phenyl | 1-azepanyl | H |
| 134 | 3,5-bis(trifluoromethyl)phenyl | 4-benzoyl-1-piperidinyl | H |
| 135 | phenyl | tetrahydroisoquinolin-1-yl | H |
| 136 | phenyl | (4-methylphenyl)amino | H |
| 137 | 3-cyanophenyl | 4-(4-chlorophenyl)-1-piperazinyl | H |
| 138 | 3-acetylphenyl | tetrahydroisoquinolin-1-yl | H |
| 139 | 3,5-bis(trifluoromethyl)phenyl | 3-(2-oxo-1-azepanyl)propylamino | H |
| 140 | 3,5-bis(trifluoromethyl)phenyl | 3-(2-oxo-1-azepanyl)propylamino | tert-butyloxycarbonyl |
| 141 | 3,5-bis(trifluoromethyl)phenyl | (3-methylbutyl)amino | cyano |
| 142 | 3,5-bis(trifluoromethyl)phenyl | (3-methylbutyl)amino | tert-butyloxycarbonyl |
| 143 | 3,5-bis(trifluoromethyl)phenyl | (3-methylbutyl)amino | (4-chlorophenyl)-sulfonyl |
| 144 | phenyl | (4-methoxybenzyl)amino | tert-butyloxycarbonyl |
| 145 | phenyl | (3-methylbutyl)amino | cyano |
| 146 | 3-cyanophenyl | N-ethyl-N-phenylamino | H |
| 147 | phenyl | (4-chlorophenyl)amino | H | and pharmaceutically acceptable salts thereof.

* * * * *